(12) United States Patent
Wakui et al.

(10) Patent No.: US 6,242,383 B1
(45) Date of Patent: Jun. 5, 2001

(54) AGRICULTURAL OR HORTICULTURAL PREPARATION WITH LIGHT STABILITY

(75) Inventors: Fujio Wakui; Haruki Mikoshiba, both of Yokohama; Kunitaka Tachibana, Tokyo-To, all of (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 09/486,539

(22) PCT Filed: Aug. 28, 1998

(86) PCT No.: PCT/JP98/03842

§ 371 Date: Feb. 29, 2000

§ 102(e) Date: Feb. 29, 2000

(87) PCT Pub. No.: WO99/11596

PCT Pub. Date: Nov. 3, 1999

(30) Foreign Application Priority Data

Aug. 29, 1997 (JP) .................................................. 9-234221

(51) Int. Cl.⁷ .......................... A01N 43/02; A01N 37/00; A01N 43/04
(52) U.S. Cl. ............................ 504/140; 504/142; 514/25; 514/510; 514/557
(58) Field of Search ............................ 514/510, 25, 557; 504/142, 140

(56) References Cited

FOREIGN PATENT DOCUMENTS

| | | |
|---|---|---|
| 49-71135 | 7/1974 | (JP) . |
| 50-58208 | 5/1975 | (JP) . |
| 51-88625 | 8/1976 | (JP) . |
| 51-95135 | 8/1976 | (JP) . |
| 51-128417 | 11/1976 | (JP) . |
| 54-117536 | 9/1979 | (JP) . |
| 62-267203 | * 11/1987 | (JP) . |
| 62-289504 | * 12/1987 | (JP) . |
| 63-79802 | * 4/1988 | (JP) . |
| 4-49239 | * 2/1992 | (JP) . |
| 5-65202 | 3/1993 | (JP) . |
| 5-117105 | * 5/1993 | (JP) . |
| 7-126211 | * 5/1995 | (JP) . |

* cited by examiner

*Primary Examiner*—Jose G. Dees
*Assistant Examiner*—Alton Pryor
(74) *Attorney, Agent, or Firm*—Wenderoth, Lind & Ponack, L.L.P.

(57) ABSTRACT

An object of the present invention is to provide an agricultural/horticultural preparation having improved photostability, comprising MK 8383 substance. A composition according to the present invention comprises a compound of formula (I):

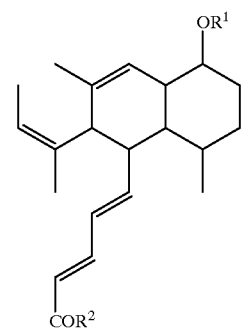

(I)

wherein $R^1$ represents hydrogen atom, or a lower alkyl or alkyl carbonyl group, and $R^2$ represents hydroxyl group or a lower alkoxy group,
or its salt, and cyclodextrins.

12 Claims, No Drawings

AGRICULTURAL OR HORTICULTURAL PREPARATION WITH LIGHT STABILITY

This application is a 371 application of PCT/JP98/03842 filed Aug. 28, 1998.

BACKGROUND OF THE INVENTION

1. Field of the Invention

The present invention relates to a composition comprising MK8383 substance and cyclodextrins, and, more particularly, to an agricultural/horticultural preparation having improved photostability.

2. Background Art

MK8383 substance which is produced by Phoma sp. T2526 strain shows high antimicrobial activity against fungi, and is also effective against fungicide resistant fungi (Japanese Patent Laid-Open Publication No. 126211/1995). MK8383substance is therefore expected as an excellent agricultural/horticultural agent.

On the other hand, Japanese Patent Laid-Open Publications No. 71135/1974, No. 149202/1980, No. 149203/1980, No. 79802/1988 and No. 291803/1995 disclose methods for improving the photostability of active components of agricultural chemicals by adding ultraviolet absorbers or forming inclusion compounds.

SUMMARY OF THE INVENTION

We have now found that MK8383 substance is poor in photostability and that it shows greatly improved photostability when it is mixed with cyclodextrins. The present invention has been accomplished based on these findings.

An object of the present invention is therefore to improve the photostability of MK8383 substance. Another object of the present invention is to provide an agricultural/horticultural preparation having improved photostability, comprising MK8383 substance.

A composition according to the present invention comprises a compound represented by the following formula (I):

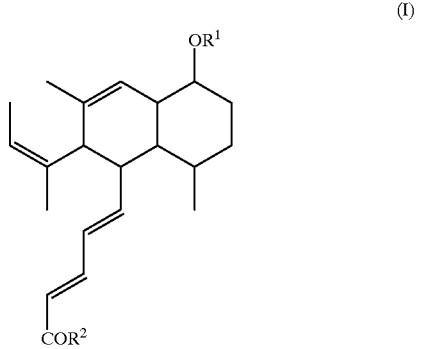

(I)

wherein $R^1$ represents hydrogen atom, or a lower alkyl or alkyl carbonyl group, and $R^2$ represents hydroxyl group or a lower alkoxy group,
or its salt, and cyclodextrins.

Deposition of Microorganism

Phoma sp. T2526 strain was deposited in National Institute of Bioscience and Human-Technology, Agency of Industrial Science and Technology (1-3, Higashi 1-chome, Tsukuba-shi, Ibaragi-ken, Japan) on Oct. 28, 1993. The accession number is FERM BP-6461.

DETAILED DESCRIPTION OF THE INVENTION

Compound of Formula (I)

The compound of formula (I) according to the present invention can be obtained, for example, by cultivating a fungus belonging to the genus Phoma, and isolating the compound from the culture. There is no particular limitation on the production fungi as long as it belongs to the genus Phoma and has the ability to produce MK8383 substance. Specific examples of such fungi include Phoma sp. T2526strain (strain T2526) isolated from fallen leaves.

Strain T2526 readily changes in its property like other fungi. Not only this strain itself but also mutants (either spontaneous or induced), plasmacyte conjugants or gene recombinants derived from this strain can also be used as the production fungi as long as they can produce MK 8383 substance. MK 8383 substance can be obtained by cultivating MK8383-producing fungi on a culture medium containing nutrients that can be utilized by ordinary microorganisms. Known nutrient sources that have conventionally been used for the cultivation of fungi can be employed in the present invention. For instance, rice, glucose, malt syrup, dextrin, starch, sugar syrup, animal or vegetable oils, and the like can be used as carbon sources. Soybean powder, wheat germ, corn steep liquor, cottonseed cake, meat extract, peptone, yeast extract, ammonium sulfate, sodium nitrate, urea and the like can be used as nitrogen sources. It is also effective to add, when necessary, inorganic salts capable of liberating such ions as sodium, potassium, calcium, magnesium, cobalt, chlorine and phosphoric or sulfuric acid ions. Further, it is also possible to properly add organic substances and/or inorganic substances capable of promoting the growth of the fungus to accelerate the production of MK 8383 substance.

Cultivation under aerobic conditions, especially solid culture or deep culture is suitable as the method of cultivation for use in the present invention. The proper cultivation temperature is from 15° C. to 35° C., and the cultivation is usually conducted at a temperature around 20° C. to 30° C. In any of solid culture, shake culture and tank culture, the accumulation amount of MK 8383 substance produced generally reaches a maximum within 2 to 14 days depending on the culture medium and conditions used. When the accumulation amount of MK 8383 substance under cultivation has reached a maximum, the cultivation is terminated, and the desired substance is isolated from the medium and purified.

To isolate MK 8383 substance from the medium after cultivation, conventional separation means such as solvent extraction, ion exchange using ion exchange resin, adsorption or partition column chromatography, gel filtration, dialysis and precipitation can be used either singly or in combination depending upon the state of the substance produced. For example, MK 8383 substance produced can be extracted from the culture with acetone-water, methanol-water, ethyl acetate, or the like. Further, MK 8383 substance accumulated in the medium can be extracted into an organic solvent layer by conducting extraction using an organic solvent immiscible with water such as butanol or ethyl acetate. MK 8383 substance thus extracted may further be purified by means of column chromatography using such an adsorbent as silica gel (e.g., "Wako Gel C-300" manufactured by Wako Pure Chemical Industries, Ltd., Japan) or alumina, or using "Sephadex LH-20" manufactured by Pharmacia AB, high performance liquid chromatography (HPLC), centrifugal separation, or the like.

Functional groups present in MK 8383 substance may be modified. For example, hydroxyl group may be etherified or acylated (e.g., acetylized); and carboxyl group may be esterified. These modifications may be conducted by conventional methods.

The term "lower alkyl" or "lower alkoxy" used in the definition of formula (I) as a group or part of a group means a linear or branched alkyl or alkoxy group having 1 to 6, preferably 1 to 4 carbon atoms.

The compound of formula (I) can form salts. Examples of these salts include alkaline metal salts such as lithium, sodium and potassium salts; alkaline earth metal salts such as magnesium and calcium salts; ammonium salts such as ammonium, methyl ammonium, dimethyl ammonium, trimethyl ammonium and dicyclohexyl ammonium salts; organic amine salts such as triethylamine, trimethylamine, diethylamine, pyridine, ethanolamine, triethanolamine, dicyclohexylamine, procaine, benzylamine, N-methylpiperidine, N-methyl morpholine and diethylaniline; and basic amino acid salts such as lysine, arginine and histidine.

Stereoisomers of the compound of formula (I) can exist, and the present invention encompasses all of these stereoisomers and mixtures thereof.

Agricultural/Horticultural Preparation

A composition according to the present invention can be obtained by mixing the compound of formula (I) with cyclodextrins. To obtain an agricultural/horticultural preparation, the compound of formula (I) may be mixed with cyclodextrins upon the formulation of the preparation. Alternatively, the compound of formula (I) can be mixed with cyclodextrins just before spraying.

Examples of cyclodextrins that can be used in the present invention include α-cyclodextrin, β-cyclodextrin, γ-cyclodextrin, methylcyclodextrin, ethylcyclodextrin, dimethylcyclodextrin and hydroxypropylcyclodextrin. Of these, γ-cyclodextrin is preferred. Any mixture of these cyclodextrins may also be used.

The composition according to the present invention may contain the cyclodextrins in an amount of 0.10 to 20 moles, preferably 0.5 to 2 moles per 1 mole of the compound of formula (I) used in the composition.

In the case where γ-cyclodextrin is used as the cyclodextrins, the composition according to the present invention may contain it in an amount of 0.10 to 5 moles, preferably 0.5 to 2 moles per 1 mole of the compound of formula (I) used in the composition.

The compound of formula (I) has strong antimicrobial activity against phytopathogenic filamentous fungi. The compound of formula (I) is particularly efficacious against gray mold, rice blast, rice sheath blight, rice bakanae disease, cucumber Fusarium wilt, tomato Fusarium wilt, grape ripe rot, and potato Verticillium wilt. The composition according to the present invention, comprising the compound of formula (I) can therefore be used as an agricultural/horticultural preparation, especially as an agricultural/horticultural biocide. The term "biocide" used herein refers to both microbicide and insecticide. The term "biocidal method" used herein includes both microbicidal method and insecticidal method.

An agricultural/horticultural preparation according to the present invention can be obtained by conventional methods for producing agrochemical preparations. Namely, by mixing the compound of formula (I) with a proper solid, liquid or gaseous carrier, surface active agents and other auxiliaries, the preparation may be obtained in any desired form selected from emulsifiable concentrate, liquid formulation, wettable powder, dust formulation, granule, oil solution, aerosol, flowable, and the like.

Examples of solid carriers include talc, bentonite, clay, kaolin, diatomaceous earth, vermiculite, white carbon and calcium carbonate. Examples of liquid carriers include alcohols such as methanol, n-hexanol and ethylene glycol, ketones such as acetone, methyl ethyl ketone and cyclohexanone, aliphatic hydrocarbons such as n-hexane, kerosine and coal oil, aromatic hydrocarbons such as toluene, xylene and methylnaphthalene, ethers such as diethyl ether, dioxane and tetrahydrofuran, esters such as ethyl acetate, nitrites such as acetonitrile and isobutyronitrile, acid amides such as dimethylformamide and dimethylacetamide, vegetable oils such as soybean oil and cottonseed oil, dimethyl sulfoxide, and water. Examples of gaseous carriers include LPG, air, nitrogen, carbonic acid gas and dimethyl ether.

Examples of surface active agents useful for dispersion, spreading or the like include alkylsulfuric esters, alkyl (aryl) sulfonates, lignin sulfonates, alkylammonium salts, alkyltrimethylammonium salts, alkylbenzyl-ammonium salts, alkylamine salts, polyoxyalkylene alkyl (aryl) ethers, polyvalent alcohol esters, sorbitan fatty acid esters, glycerin fatty acid esters, polyoxysorbitan fatty acid esters, polyoxyethylene glycerin fatty acid esters, polyoxyethylene alkyl ethers, polyoxyethylene alkylamines, sugar fatty acid esters, xanthane gum, gum arabic, carboxylmethyl cellulose, polyvinyl alcohol and sodium polyacrylate.

The carriers described above, surface-active agents and dispersants, and other auxiliary agents may be used either singly or in combination depending upon the intended use of the agricultural/horticultural preparation.

When the preparation is presented as a dust formulation, the content of MK 8383 substance in the preparation is generally from 0.1% to 30% by weight. When the preparation is in the form of a wettable powder, MK 8383 substance generally comprises 1% to 50% by weight of the preparation. Further, when the preparation takes the form of a granule, MK 8383 substance content of the preparation is generally from 0.1% to 15% by weight, and when the preparation is in the form of a flowable, generally from 1% to 40% by weight.

The agricultural/horticultural preparation according to the present invention can be used not only by spraying it over the stems or leaves of plants, but also by applying it on the surface of the soil, or into the soil. Moreover, the preparation may also be applied directly to seeds or fruits. In this case, compatible agricultural/horticultural chemicals or fertilizers may be added to the agricultural/horticultural preparation according to the present invention. Examples of such agricultural/horticultural chemicals include microbicides, insecticides, miticides, herbicides, and plant growth regulators.

The application rate of the agricultural/horticultural preparation according to the present invention may be determined depending upon the type and severity of the target disease, the type of the target crop, the target part of the crop, and the method of application including application methods ordinarily adopted in agriculture, aerial application method, and ultra low volume spray method. To spray, as a microbicide, the preparation on the stems or leaves of plants, 25 g to 200 g of the preparation in the form of an emulsifiable concentrate, wettable powder or flowable may be diluted with 25 to 500 litters of water to cover an area of 10 ares. For example, 100 g of a preparation comprising 10% by weight of MK 8383 substance may be diluted with 20 to 200 litters of water, and the whole quantity of the dilute solution can be sprayed on the plants in a field of 10 ares. When the preparation takes the form of a dust formulation, approximately 2 kg to 6 kg of the powder can be used for a field of 10 ares, for instance. Further, in the case where the preparation in the form of a granule is applied to the soil as a microbicide, approximately 2 kg to 6 kg of the preparation can be used for a field of 10 ares, for example.

EXAMPLES

The present invention will now be explained more specifically by referring to the following examples. However, the present invention is not limited by these examples.

Production Example 1: Preparation of MK 8383 Substance 40 ml of a culture medium (pH 6.0) containing 2.0% of malt syrup, 1.0% of soybean powder, 0.15% of soybean oil, 0.25% of sun grain, 0.5% of cottonseed cake, 0.0005% of $FeSO_4.7H_2O$, 0.00005% of $NiCl_2.6H_2O$, 0.00005% of $CoCl_2.6H_2O$, and 0.1% of $CaCO_3$ was put into each one of two 200-ml Erlenmeyer flasks, and sterilized in an autoclave at 121° C. for 20 minutes. To the medium autoclaved in each Erlenmeyer flask, one platinum loop of Phoma sp. T2526 strain (FERM BP-6461), MK 8383-substance-producing fungus, was inoculated, and subjected to shake culture at 210 rpm at 27° C. for 3 days.

Separately, 60 g of rice and 20 ml of tap water were put into each one of ten 500-ml Erlenmeyer flasks, and sterilized in an autoclave at 121° C. for 20 minutes. To this main fermentation medium put into in each flask, 4 ml of the seed culture obtained above was inoculated, and the resultant was allowed to stand culture at 27° C. for 14 days. The culture thus obtained was then subjected to centrifugal separation to obtain mycelia of the cultured fungus. To the mycelia was added 50% aqueous acetone (1 litter), and the mixture was stirred for 1 hour. The mycelia were filtered off to obtain 800 ml of an extract of the mycelia. After adjusting the pH of this extract to 2, the extract was centrifuged to obtain 1.83 g of a precipitate. The methanol-soluble portion of this precipitate was chromatographed on a silica gel column ("Wako gel C-200", 150 g) by using as eluents firstly chloroform/methanol (98:2) and secondly ethyl acetate/hexane (80:20) to obtain 502 mg of MK 8383 substance as a colorless powder.

The physicochemical properties and biological properties of MK 8383 substance obtained were as follows:

(1) Color and form: colorless powder
(2) Molecular formula: $C_{21}H_{30}O_3$
(3) Specific rotatory power $[\alpha]_D$ +25.70° (c=1.0, $CHCl_3$)
(4) Mass spectrum (FD-MS): m/z 330 (M)$^+$
(5) Ultraviolet absorption spectrum $\lambda_{MAX}$ MeOH nm: 205, 262
(6) Infrared absorption spectrum $\nu_{MAX}$ KBr cm$^{-1}$: 1680, 1640
(7) $^1$H NMR spectrum: in deuteromethanol, 400 MHz: 7.21 (1H, dd, J=10.9, 15.2 Hz), 6.37 (1H, dd, J=10.6, 14.1 Hz), 6.16 (1H, dd, J=10.9, 14.9 Hz), 5.77 (1H, d, J=15.1 Hz), 5.72 (1H, brs), 5.47 (1H, m), 3.68 (1H, m), 2.9 (1H, brs), 2.8 (1H, brs), 1.6–1.8 (13H, m), 1.5 (1H, m), 1.4 (1H, m), 1.1 (1H, m), 1.06 (3H, d, J=6.3 Hz)
(8) $^{13}$C NMR spectrum: in deuteromethanol, 100 MHz: 170.8, 148.3, 146.8, 136.4, 136.3, 129.5, 123.9, 123.5, 120.8, 73.2, 44.8, 43.1, 39.0, 34.0, 31.0, 30.1, 22.5, 22.3, 19.6, 13.5
(9) Solubility: soluble in chloroform, acetone, ethyl acetate and methanol, and insoluble in water
(10) Distinction between basic, acidic and neutral: acidic substance The stereostructure of MK 8383 substance according to the present invention was confirmed by the mass, UV, IR and NMR spectra of the substance, and also by the X-ray crystarographic assay of the acetate of the substance. As a result, MK 8383 substance was assumed to have the stereo-structure represented by the following formula (II):

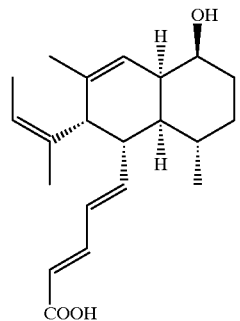

(II)

Preparation Example 1

| | |
|---|---|
| MK 8383 Substance | 10.0% by weight |
| α-Cyclodextrin | |
| (Nihon Shokuhin Kako Co., Ltd.) | 9.8% by weight |
| β-Cyclodextrin | |
| (Nihon Shokuhin Kako Co., Ltd.) | 11.5% by weight |
| γ-Cyclodextrin | |
| (Nihon Shokuhin Kako Co., Ltd.) | 13.1% by weight |
| Sodium lignin sulfonate | 3.0% by weight |
| Diatomaceous earth | 52.6% by weight |

The components above were homogeneously ground and mixed to obtain a wettable powder.

Preparation Example 2

| | |
|---|---|
| MK 8383 substance | 10.0% by weight |
| Cyclodextrin preparation | 84.0% by weight |
| (Trade name: "TB-50", Nihon Shokuhin Kako Co., Ltd.) | |
| Diatomaceous earth | 6.0% by weight |

The components above were homogeneously ground and mixed to obtain a wettable powder.

It is noted that "TB-50" consists of 13% by weight of α-cyclodextrin, 20% by weight of β-cyclodextrin, 7% by weight of γ-cyclodextrin, and 60% by weight of oligodextrin.

Preparation Example 3

| | |
|---|---|
| MK 8383 substance | 10.0% by weight |
| α-Cyclodextrin | 10.9% by weight |
| (Nihon Shokuhin Kako Co., Ltd.) | |
| β-Cyclodextrin | 16.8% by weight |
| (Nihon Shokuhin Kako Co., Ltd.) | |
| γ-Cyclodextrin | 5.9% by weight |
| (Nihon Shokuhin Kako Co., Ltd.) | |
| Sodium lignin sulfonate | 3.0% by weight |
| Diatomaceous earth | 53.4% by weight |

The components above were homogeneously ground and mixed to obtain a wettable powder.

Preparation Example 4

| | |
|---|---|
| MK 8383 substance | 10.0% by weight |
| α-Cyclodextrin (Nihon Shokuhin Kako Co., Ltd.) | 10.9% by weight |
| β-Cyclodextrin (Nihon Shokuhin Kako Co., Ltd.) | 16.8% by weight |
| γ-Cyclodextrin (Nihon Shokuhin Kako Co., Ltd.) | 5.9% by weight |
| Glycerol | 5.0% by weight |
| Begum R (Kelco Corp.) | 0.054% by weight |
| Xanthane gum (Kelco Corp.) | 0.036% by weight |
| Preservative (Trade name: "ADDAC 827", Toho Chemical Industry Co., Ltd.) | 0.005% by weight |
| Anti-foaming agent (Trade name: "PRONAL EX-300", Toho Chemical Industry Co., Ltd.) | 0.50% by weight |
| Water | 50.805% by weight |

The components above were homogeneously ground and mixed to obtain a flowable.

Test Example 1
Residual Effect Test (1)

Cyclodextrins were added to a solution of MK 8383 substance in 10% aqueous acetone, and the mixtures were diluted with water to a predetermined concentration of MK 8383 substance to obtain liquids for application.

These liquids were respectively sprayed over the cotyledons of cucumber seedlings (name of variety: Suyo) planted in planters after development of the second true leaves, and then dried in the air. The cucumber seedlings thus treated, except those ones planted in the shade condition, were directly exposed to sunlight for a predetermined period of time. Thereafter, paper discs (diameter 8 mm) that had been immersed in a suspension of the conidia of *Botrytis cinerea*, pathogen of gray mold, (resistant to benzimidazole fungicide) were placed on the cotyledons for inoculation, and the seedlings were incubated in a humid chamber at 20° C. for 3 days. The diameters of the local lesions found after this incubation were measured, and the protective value was calculated by using the following equation:

Protective value={[(the mean diameter of the local lesions in the non-treatment)−(the mean diameter of the local lesions in the treatment)]/(the mean diameter of the local lesions in the non-treatment)}×100

The results of the protection test above are shown in Table 1.

It is noted that the molar concentrations of the cyclodextrins used were calculated for the following molecular weights: the molecular weight of α-cyclodextrin=973, that of β-cyclodextrin=1135, and that of γ-cyclodextrin=1297.

TABLE 1

Gray Mold Protection Test

| MK8383 Conc. | Sunlight | Type & Concentration of Cyclodextrin | Protective Value |
|---|---|---|---|
| 0 mM | Control | 0 mM | 0 |
| 0.1 mM | Shaded | 0 mM | 100 |
| 0.1 mM | Exposure for 3 days | 0 mM | 27 |
| 0.1 mM | Exposure for 3 days | α-cyclodextrin, 0.1 mM | 40 |
| 0.1 mM | Exposure for 3 days | β-cyclodextrin, 0.1 mM | 47 |
| 0.1 mM | Exposure for 3 days | γ-cyclodextrin, 0.1 mM | 100 |
| 0.1 mM | Exposure for 3 days | α- & γ-cyclodextrins, 0.05 mM each | 97 |
| 0.1 mM | Exposure for 3 days | β- & γ-cyclodextrins, 0.05 mM each | 97 |
| 0.1 mM | Exposure for 3 days | α- & β-cyclodextrins, 0.05 mM each | 72 |
| 0.1 mM | Exposure for 3 days | α-,β- & γ-cyclodextrins, 0.033 mM each | 100 |

Test Example 2
Residual Effect Test (2)

The wettable powder prepared by the method described in Preparation Example 2 was diluted with water to 1/4,000, and, by using this dilute solution, gray mold protection test was conducted in the same manner as in Test Example 1. It is noted that a solution of MK 8383 substance in 10% aqueous acetone, diluted with water to become the same concentration for the above preparation was used for the treatment to which no cyclodextrin was applied.

The protective values were obtained by calculation in the same manner as in Test Example 1.

TABLE 2

Gray Mold Protection Test

| MK8383 Conc. | Sunlight | Type & Concentration of Cyclodextrin | Protective Value |
|---|---|---|---|
| 0 mM | Control | 0 mM | 0 |
| 0.076 mM | Shaded | 0 mM | 91 |
| 0.076 mM | Exposure for 3 days | 0 mM | 7 |
| 0.076 mM | Exposure for 3 days | 4000-fold dilute solution of Preparation Example 2 | 99 |
| 0.076 mM | Exposure for 5 days | 0 mM | 6 |
| 0.076 mM | Exposure for 5 days | 4000-fold dilute solution of Preparation Example 2 | 100 |
| 0.076 mM | Exposure for 7 days | 0 mM | 5 |
| 0.076 mM | Exposure for 7 days | 4000-fold dilute solution of Preparation Example 2 | 99 |

Test Example 3
Residual Effect Test (3)

Spraying solutions having a predetermined concentration of MK 8383 substance were prepared in the same manner as in Test Example 1, and, by using these solutions, gray mold protection test was conducted in the same manner as in Test Example 1.

The protective values were obtained by calculation in the same manner as in Test Example 1.

TABLE 3

Gray Mold Protection Test

| MK8383 Conc. | Sunlight | Type & Concentration of Cyclodextrin | Protective Value |
|---|---|---|---|
| 0 mM | Control | 0 mM | 0 |
| 0.076 mM | Shaded | 0 mM | 100 |
| 0.072 mM | Exposure for 2 days | 0 mM | 17 |

TABLE 3-continued

Gray Mold Protection Test

| MK8383 Conc. | Sunlight | Type & Concentration of Cyclodextrin | Protective Value |
|---|---|---|---|
| 0.072 mM | Exposure for 2 days | α-,β- & γ-cyclodextrins, 0.03 mM each | 36 |
| 0.072 mM | Exposure for 2 days | α-,β- & γ-cyclodextrins, 0.06 mM each | 54 |
| 0.072 mM | Exposure for 2 days | α-,β- & γ-cyclodextrins, 0.12 mM each | 84 |
| 0.072 mM | Exposure for 2 days | α-,β- & γ-cyclodextrins, 0.24 mM each | 99 |
| 0.072 mM | Exposure for 2 days | α-,β- & γ-cyclodextrins, 0.48 mM each | 99 |

What is claimed is:

1. A photo stable composition comprising a compound of formula (I):

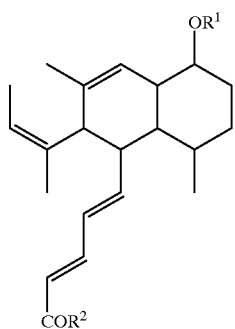

(I)

wherein $R^1$ represents hydrogen, or a lower alkyl or alkyl carbonyl group, and $R^2$ represents a hydroxyl group or a lower alkoxy group, or its salt, and at least one cyclodextrin.

2. The composition according to claim 1, wherein the at least one cyclodextrin is γ-cyclodextrin.

3. The composition according to claim 1, wherein the at least one cyclodextrin is a mixture of α-cyclodextrin, β-cyclodextrin and γ-cyclodextrin.

4. A biocidal method comprising spraying on a field a composition according to claim 1.

5. A biocidal method comprising spraying on a field a composition according to claim 2.

6. A biocidal method comprising spraying on a field a composition according to claim 3.

7. The composition according to claim 1, wherein the at least one cyclodextrin is a mixture of α-cyclodextrin and β-cyclodextrin.

8. The composition according to claim 1, wherein the at least one cyclodextrin is a mixture of α-cyclodextrin and γ-cyclodextrin.

9. The composition according to claim 1, wherein the at least one cyclodextrin is a mixture of β-cyclodextrin and γ-cyclodextrin.

10. A biocidal method comprising spraying on a field a composition according to claim 7.

11. A biocidal method comprising spraying on a field a composition according to claim 8.

12. A biocidal method comprising spraying on a field a composition according to claim 9.

* * * * *